(12) United States Patent
Liu et al.

(10) Patent No.: US 11,058,134 B2
(45) Date of Patent: Jul. 13, 2021

(54) FUNCTIONAL NUTRITIOUS RICE AND PRODUCTION METHOD THEREOF

(71) Applicant: Jiangsu Province Academy of Agricultural Sciences, Nanjing (CN)

(72) Inventors: Xianjin Liu, Beijing (CN); Ying Liang, Beijing (CN); Xiangyang Yu, Beijing (CN); Yahui Li, Beijing (CN)

(73) Assignee: JIANGSU PROVINCE ACADEMY OF AGRICULTURAL SCIENCES, Nanjing (CN)

( * ) Notice: Subject to any disclaimer, the term of this patent is extended or adjusted under 35 U.S.C. 154(b) by 555 days.

(21) Appl. No.: 15/671,773

(22) Filed: Aug. 8, 2017

(65) Prior Publication Data

US 2018/0027849 A1 Feb. 1, 2018

(30) Foreign Application Priority Data

Jan. 25, 2017 (CN) .......................... 201710056630.4

(51) Int. Cl.

| | |
|---|---|
| *A23L 7/196* | (2016.01) |
| *A23L 33/15* | (2016.01) |
| *A23L 7/10* | (2016.01) |
| *A23B 9/00* | (2006.01) |
| *A23B 7/154* | (2006.01) |
| *A23L 33/105* | (2016.01) |
| *A23L 3/349* | (2006.01) |
| *A23L 3/3544* | (2006.01) |
| *A61K 36/899* | (2006.01) |
| *A61K 47/10* | (2017.01) |
| *A61K 47/22* | (2006.01) |

(52) U.S. Cl.
CPC ............ *A23L 7/1963* (2016.08); *A23B 7/154* (2013.01); *A23B 9/00* (2013.01); *A23L 3/349* (2013.01); *A23L 3/3544* (2013.01); *A23L 7/196* (2016.08); *A23L 7/197* (2016.08); *A23L 33/105* (2016.08); *A23L 33/15* (2016.08); *A61K 36/899* (2013.01); *A61K 47/10* (2013.01); *A61K 47/22* (2013.01); *A23V 2002/00* (2013.01)

(58) Field of Classification Search
CPC ............................ A23L 7/1963; A61K 36/899
See application file for complete search history.

(56) References Cited

U.S. PATENT DOCUMENTS 4,687,669 A * 8/1987 Moritaka ................ A23L 7/101
426/309

FOREIGN PATENT DOCUMENTS

| CN | 103285964 A | * | 9/2013 |
| CN | 104687063 A | * | 6/2015 |

* cited by examiner

*Primary Examiner* — Amy L Clark
(74) *Attorney, Agent, or Firm* — Miller, Matthias & Hull LLP

(57) ABSTRACT

A nutritious rice is produced using rice, rice bran oil and a natural antioxidant as raw materials, wherein the weight ratio of the rice and rice bran oil is 1000:0.5-1000:3, and the natural antioxidant accounts for 1-15% of the weight of the rice bran oil. Such functional nutritious rice is provided with improved oxidation resistance and prolonged shelf life through the use of natural antioxidant. Also, the method of the present invention is simple, economical and effective.

2 Claims, 3 Drawing Sheets

Evaluation on Rice Processed by Different Methods

| Group | Organoleptic index | Color | Brightness | Odor | Appearance | Taste |
|---|---|---|---|---|---|---|
| Processed | Example 1 | White | Bright and glossy | Strong | Complete | |
| | Without treatment with rice bran oil | White | Lusterless | Flat | Complete | |
| Steamed | Example 1 | White | Bright and glossy | Strong | Complete and full | Smooth and chewy |
| | Without treatment with rice bran oil | White | Lusterless | Flat | Complete and full | Coarse and hard |

FIG. 1

Measurement of Nutritional Ingredients in Rice Processed by Different Methods

| Nutritional Ingredients / Group | Total polyphenols (mg/kg) | Catechins (mg/kg) | Vitamin C (mg/kg) | Unsaturated fatty acids (mg/kg) | Oleic acid (mg/kg) | Linoleic acid (mg/kg) | Phytosterol (mg/kg) | Oryzanol (mg/kg) |
|---|---|---|---|---|---|---|---|---|
| Example 2 | 71 | 38 | 34 | 734 | 246 | 153 | 52 | 11 |
| Without treatment with rice bran oil | 0 | 0 | 21 | 289 | 59 | 31 | 12 | 1 |

FIG. 2

Measurement of Anti-oxidation Performance of Rice Processed with Different Rice Bran Oils

| Group | Processing Time (hour) | 0 | 24 | 48 | 72 | 96 | 120 | 144 | 168 |
|---|---|---|---|---|---|---|---|---|---|
| Peroxide value (meq/kg) | Example 1 | 0 | 0.23 | 0.18 | 0.34 | 0.14 | 0.5 | 0.34 | 0.5 |
| | Without tea polyphenol and vitamin C | 0 | 0.98 | 2.05 | 4.13 | 5.34 | 6.87 | 7.32 | 8.6 |

FIG. 3

FUNCTIONAL NUTRITIOUS RICE AND PRODUCTION METHOD THEREOF

TECHNICAL FIELD

The present invention relates to the field of food and in particular to a functional nutritious rice and a method for producing the same.

BACKGROUND

Originated in China and can be found in most places of the world except Antarctica, rice plant is one of the world's major food crops. Rice is obtained from grains after a series of processes including cleaning, hulling, milling, polishing, packing etc. About 60%-70% of the vitamins, minerals and a large number of essential amino acids are concentrated in the overlying tissue of the rice. Most of the nutrients are removed along with the hull and endosperm during the processing, with most of the remnant being carbohydrates and some proteins.

Rice bran, the main byproduct of grain processing, mainly includes the grain's pericarp, testa perisperm, aleurone layer, embryo etc. Domestic and foreign research and data show that rice bran is rich in nutrients and physiologically active substances with high nutritional and economic value. Rice bran oil is a kind of rice oil prepared by squeezing or leaching of the rice bran. Rich in nutrients such as oleic acid, linoleic acid, oryzanol, vitamin E, sitosterol and other phytosterols, rice bran oil helps remove blood cholesterol, reduces blood lipids, promote blood circulation and human growth and development, and regulate endocrine and autonomic nerve etc. In addition, rice bran oil has a special aromatic odor having a positive influence on high-temperature resistance, extending shelf life of food, and improving the food stability.

How to improve the nutritional value of rice and meet consumers' demand for nutrients is the main concern in today's rice processing industry. In addition, oxidative deterioration, short shelf life and difficulty in rice storage of the rice on the market are urgent problems to be solved.

SUMMARY

It is an object of the present invention to overcome the above shortcomings in a simple, economic and effective manner by providing a functional nutritious rice which enhances the oxidation resistance and prolongs the shelf life using a natural antioxidant.

It is another object of the present invention to provide a method for producing such functional nutritious rice.

The object of the present invention is achieved by the following.

A functional nutritious rice is produced using rice, rice bran oil and a natural antioxidant as raw materials, wherein the weight ratio of the rice and rice bran oil is 1000:0.5-1000:3, and the natural antioxidant accounts for 1-15% of the weight of the rice bran oil.

The method of producing such functional nutritious rice comprises the following steps:

1) subjecting the grains to impurity removal, detritus removal, magnetic separation, husking, and husked rice separation to obtain brown rice, followed by subjecting the brown rice to milling, grading sieve passing and rice cooling to obtain peeled brown rice;

2) subjecting the peeled brown rice to a first polishing using water as the polishing agent and a second polishing using rice bran oil as the polishing agent, obtaining a rice;

3) adding rice bran oil to the rice after the second polishing, stirring the same evenly, keeping the mixture still for oil impregnation at 15-20° C. in a dark place while performing ultrasonic treatment on the same, wherein the amount of the rice bran oil used is 0.5-3 grams per kg of the rice, and wherein the rice bran oil is added with a natural antioxidant accounting for 1-15% of the weight of the rice bran oil.

The natural antioxidant comprises one or more selected from a group consisting of vitamin, tea polyphenol, β-carotene, rosemary extract, capsorubin, and lycopene.

The vitamin is vitamin C or vitamin E, or a mixture thereof.

Preferably, the functional nutritious rice is produced using rice, rice bran oil, tea polyphenol and vitamin C as the raw materials, wherein the weight ratio of the rice and the rice bran oil is 1000:0.5-1000:3, and wherein the naturally extracted tea polyphenol and vitamin C account for 3-8% and 0.5-3% of the weight of the rice bran oil, respectively. Preferably, the vitamin C is present in the form of vitamin C palmitate and the tea polyphenol is present in the form of tea polyphenol palmitate.

The rice is obtained by polishing the peeled brown rice twice using water and rice bran oil as the polishing agent, respectively. The rice bran oil is added with tea polyphenol and vitamin C, which account for 3-8% and 0.5-3% of the weight of the rice bran oil, respectively. Preferably, the vitamin C is present in the form of vitamin C palmitate and the tea polyphenol is present in the form of tea polyphenol palmitate.

As the polishing agent, the water is used as the polishing agent in an amount of 6-9 grams per kg of the peeled brown rice, and the rice bran oil is used as the polishing agent in an amount of 0.5-1.5 grams per kg of the peeled brown rice.

The method of producing such functional nutritious rice comprises the following steps:

1) subjecting the grains to impurity removal, detritus removal, magnetic separation, husking, and husked rice separation to obtain brown rice, followed by subjecting the brown rice to milling, grading sieve passing and rice cooling to obtain peeled brown rice;

2) subjecting the peeled brown rice to a first polishing using water as the polishing agent and a second polishing using rice bran oil as the polishing agent, obtaining a rice;

3) adding rice bran oil to the rice after the second polishing, stirring the same evenly, keeping the mixture still for oil impregnation at 15-20° C. in a dark place while performing ultrasonic treatment on the same, wherein the amount of the rice bran oil used is 0.5-3 grams per kg of the rice, and wherein the rice bran oil is added with tea polyphenol and vitamin C, which account for 3-8% and 0.5-3% of the weight of the rice bran oil, respectively; preferably, the vitamin C is present in the form of vitamin C palmitate and the tea polyphenol is present in the form of tea polyphenol palmitate.

The purpose of the husked rice separation is to obtain the net brown rice and the purpose of passing the grading sieve is to remove the cracked or broken rice.

Preferably, the milling is carried out by light grinding and multi-mill using a four-roller rice mill. The use of the four-roller rice mill can reduce the occurrence of broken rice, ensure the rice milling degree, increase the rice yield and reduce the milling temperature.

After the milling and grading, the brown rice is cooled to 20-25° C. Such rice cooling can prevent the oxidation and microbial growth on the surface caused by high temperature.

The amount of the water used as the polishing agent is 6-9 grams per kg of the peeled brown rice. If the amount of water used is too small, it is difficult to remove the rough skin of the brown rice and at the same time the polishing temperature would be relatively high. If the amount of water used is too high, the water content of the rice would be increased, leading to the risk of mildew.

The rice bran oil used for the second polishing is 0.5-1.5 grams per kg of the peeled brown rice. If the amount of rice bran oil used is too small, the rice surface cannot be evenly coated with the oil to obtain surface smoothness and brightness. If the amount of rice bran oil used is too high, the surface oil would be too much, causing rice conglutination.

The rice bran oil used as the polishing agent is added with naturally extracted tea polyphenol and vitamin C, which account for 3-8% and 0.5-3% of the weight of the rice bran oil, respectively. Preferably, the vitamin C is present in the form of vitamin C palmitate and the tea polyphenol is present in the form of tea polyphenol palmitate, increasing their solubility in the oil such that they can easily impregnate into the rice.

Using rice bran oil as the polishing agent for the second polishing has the following advantages:

1) Increasing nutritional ingredients, promoting the fragrance of rice and improving its organoleptic quality;

2) Rendering the rice surface smooth, bright and glossy; and

3) Forming an oil film on the rice surface, which facilitates oil adhesion and impregnation for later steps in preparation for oil impregnation.

The purpose of oil impregnation is to enable the tea polyphenol, vitamin C and rice bran oil to impregnate into the rice in order to further increase the nutritional ingredients. The amount of the rice bran oil used for the oil impregnation is 0.5-3 grams per kg of the brown rice. If the amount of rice bran oil used is too small, the tea polyphenol and vitamin C cannot reach the center of the rice. As a result, the rice cannot obtain enough brightness, fragrance and nutritional ingredients. If the amount of rice bran oil used is too high and exceeds the absorption capacity of the rice, the oil on the surface of the rice would be too much, causing rice conglutination and poor appearance.

The rice bran oil used for oil impregnation is added with tea polyphenol and vitamin C, which account for 3-8% and 0.5-3% of the weight of the rice bran oil, respectively. A good anti-oxidation effect can be produced from the synergy of said tea polyphenol and vitamin C in the specified concentration range. If the amount of tea polyphenol added into the rice bran oil is too small, the surface area of the oil coated onto the rice increases and the anti-oxidation effect would be poor, at the same time, it cannot reach the center of the rice. If the amount of tea polyphenol added is too high, the rice will be given a bitter taste thus the taste of the rice would be affected. If the amount of vitamin C added into the rice bran oil is too small, the surface area of the oil coated onto the rice increases and the anti-oxidation effect would be poor. If the amount of vitamin C added is too high, physical discomfort may arise.

Therefore, adding tea polyphenol and vitamin C into the rice bran oil has the following advantages:

1) increasing oxidation resistance of the oil, prolonging the shelf life of the rice, increasing the rice's nutritional ingredients and functional activity, and providing the rice with excellent color, fragrance and taste;

2) the good oxidation resistance could be achieved by the co-existence of them, which imparts the oil with good oxidation resistance; and 3) improving the oil's oxidation resistance due to the addition of vitamin C into the rice bran oil and preventing oxidation of the tea polyphenol since the oil containing vitamin C inhibits the contact between oxygen and tea polyphenol.

The tea polyphenol and vitamin C are added to the rice bran oil and then the rice is subjected to polishing and oil impregnation. Using the oil as a carrier, the tea polyphenol and vitamin C can be better adhered to and absorbed by the rice such that they can impregnate into the rice.

After oil impregnation, preferably, the rice is kept still for 3-4 hours, with the rice being stirred every half hour. The ultrasonic treatment is carried out following each stirring operation. The ultrasonic treatment lasts for 15-20 minutes at a power of 100-200 w. The purpose of keeping still and stirring is to make the rice bran oil, tea polyphenol and vitamin C to sufficiently impregnate into the rice in order to avoid oxidation on and loss from the surface. The ultrasonic treatment increases the speed of the rice bran oil impregnating into the rice and reduces the impregnation time.

Keeping the rice still at 15-20° C. in a dark place can prevent degradation of the tea polyphenol and vitamin C, as well as oxidation of the rice bran oil due to the light and heat.

Preferably, the rice is stored in a dark place at a temperature of no higher than 25° C.

As compared with the prior art, the present invention has the advantageous effects explained below.

According to the method of the present invention, the rice is subjected to polishing the second time using rice bran oil containing naturally extracted tea polyphenol and vitamin C, followed by oil impregnation, whereby the rice is provided with significantly improved organoleptic quality such as smoothness, brightness, fragrance etc. Adding rice bran oil containing tea polyphenol and vitamin C into the rice restores the grain's own nutritional ingredients, significantly increases the polished rice's nutritional ingredients and functional activity and improves its nutritional quality. Adding naturally extracted tea polyphenol and vitamin C into the rice bran oil improves the rice's oxidation resistance, at the same time, the naturally extracted tea polyphenol and vitamin C carried by the rice bran oil can be better impregnated into and absorbed by the rice. Using the natural antioxidants increases the rice's oxidation resistance and prolongs its shelf life. The method according to the present invention is simple, economic and effective.

BRIEF DESCRIPTION OF THE DRAWINGS

While the appended claims set forth the features of the present techniques with particularity, these techniques, together with their objects and advantages, may be best understood from the following detailed description taken in conjunction with the accompanying drawings of which:

FIG. 1 is a chart showing an evaluation of rice prepared by different methods;

FIG. 2 is a chart showing measurement of nutritional content in rice processed by different methods; and FIG. 3 is a chart showing measurement of anti-oxidation performance of rice processed with different rice bran oils;

DETAILED DESCRIPTION OF THE INVENTION

The present invention will now be described in further details with reference to the examples given by the inventors.

Note that the tea polyphenol (content≥70%) is a fat-soluble tea polyphenol purchased from Xi'an Changyue Phytochemistry Technology Co., Ltd., and the vitamin C palmitate is purchased from Wuhan Jiangmin Huatai Pharmaceutical Chemical Technology Co., Ltd.

Example 1

100 kg of Nanjing 46 grains was used. The grains were subjected to impurity removal, detritus removal, magnetic separation, husking, and husked rice separation to obtain brown rice, followed by subjecting the brown rice to light grinding and multi-mill with a four-roller rice mill, grading sieve to remove cracked rice and broken rice, and cooling the rice to 20° C., whereby about 90 kg of peeled brown rice was obtained. 810 grams of water was drop-wise introduced as a polishing agent to polish the peeled brown rice. Thereafter, 135 grams of rice bran oil (added with tea polyphenol and vitamin C palmitate, which account for 3% and 3% of the weight of the rice bran oil, respectively) was drop-wise introduced as a polishing agent to give a second polishing to the peeled brown rice. Again, 270 grams of rice bran oil (added with tea polyphenol and vitamin C palmitate, which account for 3% and 3% of the weight of the rice bran oil, respectively) was added into the polished rice, the mixture was stirred evenly, kept still in a dark place at 15-20° C. for 4 hours, wherein the mixture was stirred every half hour while receiving ultrasonic treatment at a power of 100 w for 20 minutes. The rice impregnated with oil was passed through two color sorters to remove the rice of undesired colors, chalky rice and broken rice. The sorted and purified rice was vacuum packed and stored in a dark place at 0° C.

The rice produced according to above example was tested and show the following test indexes:
1. Organoleptic index
   Color: white
   Brightness: glittering and translucent, glossy
   Odor: strong rice fragrance
   Appearance: complete
2. Quality index
   Broken rice≤2.5%; incomplete rice≤3.0%; taste score≥90%; maximum impurity≤0.25%; rice bran powder≤0.25%; rice grains≤4.0%; water content≤15%.

The respective indexes meet GB1354-2009.

Example 2

200 kg of Nanjing 9108 grains was used. The grains were subjected to impurity removal, detritus removal, magnetic separation, husking, and husked rice separation to obtain brown rice, followed by subjecting the brown rice to light grinding and multi-mill with a four-roller rice mill, grading sieve to remove cracked rice and broken rice, and cooling the rice to 25° C., whereby about 185 kg of peeled brown rice was obtained. 1110 grams of water was drop-wise introduced as a polishing agent to polish the peeled brown rice. Thereafter, 92.5 grams of rice bran oil (added with tea polyphenol and vitamin C palmitate, which account for 8% and 0.5% of the weight of the rice bran oil, respectively) was drop-wise introduced as a polishing agent to give a second polishing to the peeled brown rice. Again, 92.5 grams of rice bran oil (added with tea polyphenol and vitamin C palmitate, which account for 8% and 0.5% of the weight of the rice bran oil, respectively) was added into the polished rice, the mixture was stirred evenly, kept still in a dark place at 15-20° C. for 3 hours, wherein the mixture was stirred every half hour while receiving ultrasonic treatment at a power of 200 w for 15 minutes. The rice impregnated with oil was passed through two color sorters to remove the rice of undesired colors, chalky rice and broken rice. The sorted and purified rice was vacuum packed and stored in a dark place at 10° C.

The rice produced according to above example was tested and show the following test indexes:
1. Organoleptic index
   Color: white
   Brightness: glittering and translucent, glossy
   Odor: strong rice fragrance
   Appearance: complete
2. Quality index
   Broken rice≤2.5%; incomplete rice≤3.0%; taste score≥90%; maximum impurity≤0.25%; rice bran powder≤0.25%; rice grains≤4.0%; water content≤15%.

The respective indexes meet GB1354-2009.

The effects of the present invention will be further described below by way of some experimental examples.

Experimental Example 1

Differences in organoleptic quality of the rice processed in various ways were studied.

Nanjing 46 was respectively processed according to the method described in Example 1 and a method similar to that described in Example 1 except that it does not include polishing and impregnation with the rice bran oil. Sensory evaluation was performed on the processed rice and the steamed rice (the ratio of rice and water was 1:1.1). The evaluation results are shown in FIG. 1.

According to FIG. 1, the rice processed according to Example 1 is white, bright, and glossy and has strong fragrance. The rice cooked has brightness, strong fragrance, and smooth and chewy taste. It is obvious that the rice processed according to Example 1 has better organoleptic quality than rice processed without treatment using the rice bran oil.

Experimental Example 2

Differences in nutritional ingredients of the rice processed in various ways were studied.

Nanjing 9108 was respectively processed according to the method described in Example 2 and a method similar to that described in Example 2 except that it does not include polishing and impregnation with the rice bran oil. Measurement was performed on the content of total polyphenols, catechins, vitamin C, total unsaturated fatty acids, oleic acid, linoleic acid, phytosterol and oryzanol in the processed rice.

The measurement on total polyphenols was performed according to GB/T 31740.2-2015; the measurement on catechins was performed according to GB/T 8313-2008, the measurement on vitamin C was performed according to GB/T 6195-1986, the measurement on total unsaturated fatty acids, oleic acid and linoleic acid was performed according to GB 19112-2003, the measurement on phytosterols the measurement on GB/T 25223-2010; and the measurement on oryzanol was performed according to *Improvement of Method for Determination of Oryzanol Content* (Liu Lanying et al, Heilongjiang Liang Shi, 2004, vol 06,P 37-38). The results are shown in FIG. 2.

As shown in FIG. 2, it is obvious that the content of nutritional ingredients in rice processed according to Example 2 is higher than that of the nutritional ingredients in rice processed without treatment with rice bran oil.

Experiment Example 3

Differences in oxidation resistance of the rice caused by the addition of tea polyphenol and vitamin C into the rice bran oil were studied.

Wuchang rice was respectively processed according to the method described in Example 1 and a method similar to that described in Example 1 except that the rice bran oil used for polishing and oil impregnation does not contain tea polyphenol and vitamin C. The anti-oxidation performance of the processed rice was studied.

Measurement method: the processed rice was placed in an incubator at 35° C. and exposed to the air, and its peroxide value was measured every 24 hours. The measurement of the peroxide value was performed according to *Improvement of Method for Determination of Acid Value and Peroxide Value in Nuts* (Song Jinhua, Modern Preventive Medicine, 2006, vol 33, P 578-579).

It can be seen that the rice processed according to Example 1 has better oxidation resistance, while the rice processed with rice bran oil containing no tea polyphenol and vitamin C is easily oxidized, as shown in FIG. 3.

We claim:

1. A method of producing a functional nutritious rice, wherein the method comprises the following steps:
   (1) subjecting rice grains to impurity removal, detritus removal, magnetic separation, husking, and husked rice separation to obtain brown rice, followed by subjecting the brown rice to milling, grading sieve passing and rice cooling to obtain peeled brown rice, wherein the milling is carried out by light grinding and multi-mill using a four-roller rice mill, wherein after the milling and grading, the brown rice is cooled to 20-25° C.;
   (2) subjecting the peeled brown rice to a first polishing using water as the polishing agent and a second polishing using rice bran oil as the polishing agent, obtaining a polished rice, wherein the water is used as the polishing agent in an amount of 6-9 grams per kg of the peeled brown rice; and
   (3) adding rice bran oil to the polished rice after the second polishing, stirring the same evenly, keeping the mixture still for oil impregnation at 15-20° C. in a dark place while performing ultrasonic treatment on the same, wherein the amount of the rice bran oil used is 0.5-1.5 grams per kg of the peeled brown rice, and wherein the rice bran oil is added with tea polyphenol and vitamin C, which account for 3-8% and 0.5-3% of the weight of the rice bran oil, respectively.

2. The method of producing the functional nutritious rice according to claim 1, wherein the rice is kept still for 3-4 hours, except for the rice being stirred every half hour; and wherein the ultrasonic treatment is carried out for 15-20 minutes at a power of 100-200 w following each stirring operation.

* * * * *